United States Patent [19]

Brooks et al.

[11] Patent Number: 5,750,558
[45] Date of Patent: May 12, 1998

[54] OXIME DERIVATIVES OF INDOLE AND INDENE COMPOUNDS AS INHIBITORS OF PROSTAGLANDIN BIOSYNTHESIS

[75] Inventors: Clint D. W. Brooks, Libertyville; Teodozyj Kolasa, Lake Villa, both of Ill.; Wendy Lee, Hamden, Conn.; Andrew O. Stewart, Libertyville, Ill.

[73] Assignee: Abbott Laboratories, Abbott Park, Ill.

[21] Appl. No.: 660,048

[22] Filed: Jun. 6, 1996

[51] Int. Cl.$^6$ .................. A61K 31/40; C07D 209/14
[52] U.S. Cl. .................. 514/415; 514/314; 514/365; 514/367; 514/382; 514/561; 546/174; 548/159; 548/181; 548/252; 548/505; 562/428
[58] Field of Search .................. 514/314, 365, 514/367, 382, 415, 561; 546/174; 548/159, 181, 252, 505; 562/428

[56] References Cited

U.S. PATENT DOCUMENTS

| | | | |
|---|---|---|---|
| 2,930,798 | 3/1960 | Schmitt | 548/505 |
| 3,055,912 | 9/1962 | Hoffmann | 548/505 X |
| 5,399,699 | 3/1995 | Kolasa et al. | 546/174 |

FOREIGN PATENT DOCUMENTS

| | | | |
|---|---|---|---|
| 1935301 | 2/1970 | Germany | 548/505 |
| 9203132 | 3/1992 | WIPO . | |

OTHER PUBLICATIONS

J. A. Mitchell et al., "Cyclooxygenase-2: Regulatory and Relevance in Inflamation," *Biochemical Pharmacology*, vol. 50, No. 10 (1995), 1535-1542.

B. Battistini et al., COX-1 and COX-2: Toward the Development of More Selective NSAIDs *Drug News and Perspectives*, vol. 7, No. 8 (1994) 501-512.

D. L. DeWitt et al., "The Differential of Prostaglandin Endoperoxide H Synthases-1 and -2 to Nonsteroidal Anti-Inflamatory Drugs: Aspirin Derivatives as Selective Inhibitors," *Medicinal Chemistry Research*, vol. 5, No. 5, (1995) 325-343.

*Primary Examiner*—Johann Richter
*Assistant Examiner*—Laura L. Stockton
*Attorney, Agent, or Firm*—Frank Z. Yang

[57] ABSTRACT

Described herein are compounds having the formula

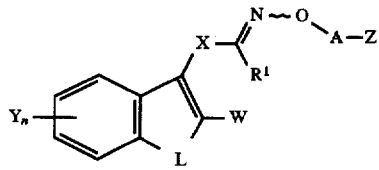

or a pharmaceutically acceptable salt thereof wherein L is selected from the group consisting of

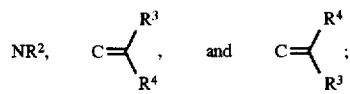

$R^2$ is selected from (a)

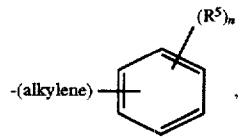

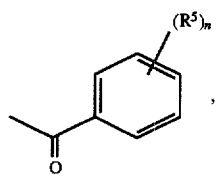

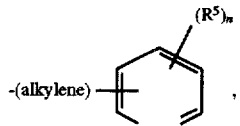

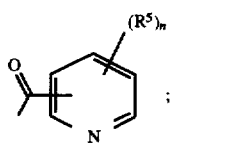

$R^3$ is selected from optionally substituted phenyl, and optionally substituted pyridyl; Y is selected from halogen, alkyl, haloalkyl, alkoxy, pyridylmethoxy, thiazolylmethoxy, benzothiazolylmethoxy, quinolylmethoxy, and optionally substituted quinolylmethoxy; W is selected from hydrogen, alkyl, hydroxyalkyl, and hydroxy; A is absent or is selected from optionally substituted alkylene optionally substituted cycloalkylene, optionally substituted cycloalkylene wherein one or two of the carbon atoms is replaced with one or two heteroatoms independently selected from O, S, and N, and

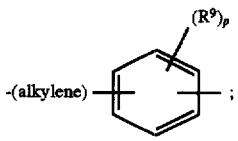

and X is absent or is alkylene; Z is selected from (a) hydrogen, (b) COM wherein M is selected from (b-1) a pharmaceutically acceptable metabolically cleavable group, (b-2)—$OR^{10}$,(b-3)—$O(CH_2)_n$—$CH(OR^{12})$—$CH_2OR^{13}$, and (b-4)—$NR^{15}R^{16}$(c)—$OR^{17}$, (d) tetrazolyl, (e)—CH($OR^{17}$)—$CH_2OR^{18}$,(f)—CH($OR^{17}$)—$CH_2$—$CH_2OR^{18}$, (g)—CH($OR^{17}$)—CH($OR^{18}$)—$CH_2OR^{19}$, and (h)=N—$OR^{17}$; and $R^1$ and $R^4$ selected from (a) hydrogen, (b) alkyl, and (c) optionally substituted phenyl, are prostaglandin biosynthesis inhibitors and are useful in the treatment of inflammatory disease states. Also disclosed are prostaglandin inhibiting compositions, and a method of inhibiting prostaglandin biosynthesis in a mammal.

16 Claims, No Drawings

OXIME DERIVATIVES OF INDOLE AND INDENE COMPOUNDS AS INHIBITORS OF PROSTAGLANDIN BIOSYNTHESIS

TECHNICAL FIELD

This invention relates to novel compounds having activity to inhibit prostaglandin biosynthesis, to pharmaceutical compositions comprising these compounds and to a medical method of treatment. More particularly, this invention concerns oxime containing derivatives of indole and indane compounds which inhibit prostaglandin biosynthesis, particularly the induced prostaglandin endoperoxide H synthase (PGHS-2, cyclooxygenase-2, COX-2), to pharmaceutical compositions comprising these compounds and to a method of inhibiting prostaglandin biosynthesis.

BACKGROUND OF THE INVENTION

The prostaglandins are extremely potent substances which produce a wide variety of biological effects, often in the nanomolar to picomolar concentration range. The discovery of two forms of prostaglandin endoperoxide H synthase, PGHS-1 and PGHS-2, that catalyze the oxidation of arachidonic acid leading to prostaglandin biosynthesis has resulted in renewed research to delinate the role of these two isozymes in physiology and pathophysiology. These isozymes have been shown to have different gene regulation and represent distinctly different prostaglandin biosynthesis pathways. The PGHS-1 pathway is expressed constitutively in most cell types. It responds to produce prostaglandins that regulate acute events in vascular homeostasis and also has a role in maintaining normal stomach and renal function. The newly discovery PGHS-2 pathway involves an induction mechanism which has been liked to inflammation, mitogenesis and ovulation phenomena.

Prostaglandin inhibitors provide therapy for pain, fever, and inflammation, and are useful therapies, for example in the treatment of rheumatoid arthritis and osteoarthritis. The non-steroidal antiinflammatory drugs (NSAIDs) such as ibuprofen, naproxen and fenamates inhibit both isozymes, prostaglandin endoperoxide H synthase 1 (PGHS-1) and prostaglandin endoperoxide H synthase 2 (PGHS-2). Inhibition of the constitutive enzyme PGHS-1 results in gastrointestinal side effects including ulcers and bleeding and incidence of renal problems with chronic therapy. Inhibitors of the induced isozyme PGHS-2 are proposed to provide antiinflammatory activity without the side effects of PGHS-1 inhibitors. A general review of the current knowledge of PGHS-1 and PGHS-2 isozyme properties and a summary of inhibitors and their activity is provided by:

(1) Battistini, B.; Botting, R.; Bakhle, Y. S. COX-1 and COX-2: toward the development of more selective NSAIDs, Drug New and Perspectives 1994, 7(8), 501-512.

(2) DeWitt, D. L.; Bhattacharyya, D.; Lecomte, M.; Smith, W. L. The differenctial susceptibility of prostaglandin endoperoxide H synthases-1 and-2 to nonsteroidal anti-inflammatory drugs: aspirin derivatives as selective inhibitors. Med. Chem. Res. 1995, 5(5), 325-343.

(3) Mitchell, J. A.; Larkin, S.; Williams, T. J. Cyclooxygenase-2: regulation and relevance in inflammation. Biochem. Pharm. 1995, 50(10), 1535-1542.

Indomethacin and sulidac were discovered to be prostaglandin biosynthesis inhibitors prior to the discovery of the different isozyme forms. Indomethacin and sulindac are reported to inhibit both PGHS-1 and PGHS-2 (Battistini, B.; Botting, R.; Bakhle, Y. S. COX-1 and COX-2: toward the development of more selective NSAIDs, Drug New and Perspectives 1994, 7(8), 501-512.)

SUMMARY OF THE INVENTION

In its principal embodiment, the present invention provides certain novel oxime containing derivatives of indole and indane compounds with unexpected preferrential inhibitory activity against the induced PGHS-2 isozyme versus PGHS-1 which are useful in the treatment of allergic and inflammatory disease states in which the prostaglandins play a role.

The compounds of the present invention have the structure

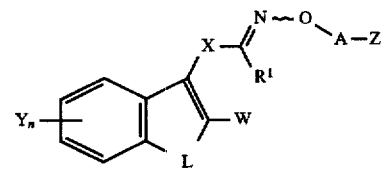

or a pharmaceutically acceptable salt thereof wherein L is selected from the group consisting of

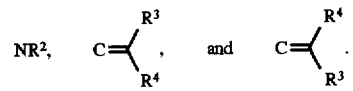

$R^2$ is selected from the group consisting of

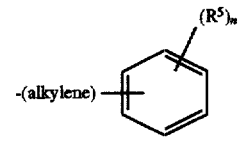

(a)

wherein the alkylene portion is of one to six carbon atoms, n is 0, 1, 2,or 3, and $R^5$, which may be the same or different at each occurrence, is selected from —$OR^6$, —$SR^6$, halogen, alkyl of one to six carbon atoms, haloalkyl of one to six carbon atoms, and alkoxy of one to six carbon atoms, (b)

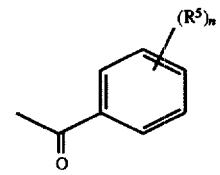

wherein $R^5$ and n are defined above, (c)

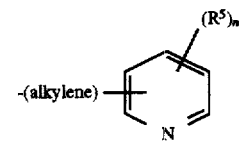

wherein the alkylene portion is of one to six carbon atoms, and $R^5$ and n are defined above, and (d)

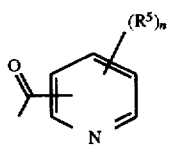

wherein $R^5$ and n are defined above;

$R^3$ is selected from the group consisting of (a) phenyl, (b) phenyl substituted with 1, 2, or 3 groups independently selected from —$OR^7$, —$SR^7$, halogen, alkyl of one to six carbon atoms, haloalkyl of one to six carbon atoms, and alkoxy of one to six carbon atoms, (c) pyridyl, and (d) pyridyl substituted with 1, 2, or 3 groups independently selected from —$OR^7$, —$SR^7$, halogen, alkyl of one to six carbon atoms, haloalkyl of one to six carbon atoms, and alkoxy of one to six carbon atoms.

Y is selected from the group consisting of (a) halogen, (b) alkyl of one to six carbon atoms, (c) haloalkyl of one to six carbon atoms, (d) alkoxy of one to six carbon atoms, (e) pyridylmethoxy, (f) thiazolylmethoxy, (g) benzothiazolylmethoxy, (h) quinolylmethoxy, and (i) quinolylmethoxy substituted with one or two substitutents selected from halogen and haloalkyl of one to six carbon atoms, and n is 0, 1, 2, or 3.

W is selected from the group consisting of (a) hydrogen, (b) alkyl of one to six carbon atoms, (c) hydroxyalkyl of one to six carbon atoms, and (d) hydroxy.

A is absent or is selected from the group consisting of (a) alkylene of one to six carbon atoms, (b) alkylene of one to six carbon atoms substituted with one or two substituents selected from the group consisting of —$OR^8$, and —$COOR^8$, (d) cycloalkylene of three to eight carbon atoms, (e) cycloalkylene of three to eight carbon atoms substituted with one or two substituents independently selected from alkyl of one to six carbon atoms, —$OR^8$, and —$COOR^8$, (f) cycloalkylene of three to eight carbon atoms wherein one or two of the carbon atoms is replaced with one or two heteroatoms independently selected from O, S, and N, (g) cycloalkylene of three to eight carbon atoms wherein one or two of the carbon atoms is replaced with one or two heteroatoms independently selected from O, S, and N, and the ring contains one or two substituents independently selected from alkyl of one to six carbon atoms, —$OR^8$, and —$COOR^8$, and (h)

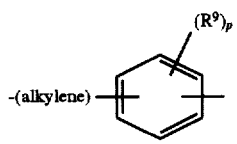

wherein the alkylene portion is of one to six carbon atoms, p is 0, 1, 2, or 3, and $R^9$, which may be the same or different at each occurrence, is selected from —$OR^8$, —$COOR^8$, halogen, alkyl of one to six carbon atoms, haloalkyl of one to six carbon atoms, and alkoxy of one to six carbon atoms.

X is absent or is alkylene of one to six carbon atoms.

Z is selected from the group consisting of (a) hydrogen, (b) COM wherein M is selected from the group consisting of (b-1) a pharmaceutically acceptable metabolically cleavable group, (b-2) —$OR^{10}$ wherein $R^{10}$ is selected from the group consisting of (b-2-a) a pharmaceutically acceptable cation, (b-2-b) hydrogen, (b-2-c) alkyl of one to six carbon atoms, (b-2-d) phenyl, and (b-2-e) phenyl substituted one, two or three substituents selected from the group consisting of halogen, alkyl of one to six carbon atoms, haloalkyl of one to six carbon atoms, and alkoxy of one to six carbon atoms, and

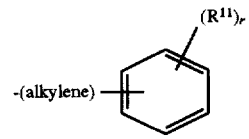

wherein the alkylene portion is of one to six carbon atoms, r is 0, 1, 2, or 3, and $R^{11}$, which may be the same or different at each occurrence, is selected from halogen, alkyl of one to six carbon atoms, haloalkyl of one to six carbon atoms, and alkoxy of one to six carbon atoms, (b-3) —$O(CH_2)_w$—$CH(OR^{12})$—$CH_2OR^{13}$ wherein w is 1, 2, or 3, $R^{12}$ and $R^{13}$ are independently selected from the group consisting of (b-3-a) hydrogen, (b-3-b) alkyl of one to six carbon atoms, (b-3-c) phenyl, and (b-3-d) phenyl substituted one, two or three substituents selected from halogen, alkyl of one to six carbon atoms, haloalkyl of one to six carbon atoms, alkoxy of one to six carbon atoms, and

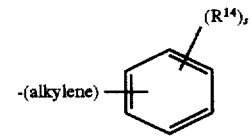

wherein the alkylene portion is of one to six carbon atoms, s is 0, 1, 2, or 3, and $R^{14}$, which may be the same or different at each occurrence, is selected from halogen, alkyl of one to six carbon atoms, haloalkyl of one to six carbon atoms, and alkoxy of one to six carbon atoms, or $R^{12}$ and $R^{13}$ together with the oxygen atoms to which they are attached define a 5-or 6-membered heterocyclic ring which may be optionally substituted with one or two substituents selected from alkyl of one to six carbon atoms, haloalkyl of one to six carbon atoms, and alkoxy of one to six carbon atoms, and (b-4)—$NR^{15}R^{16}$ wherein $R^{15}$ and R16 are independently selected from hydrogen, alkyl of one to six carbon atoms, hydroxyalkyl of one to six carbon atoms, and hydroxy, (c)—$OR^{17}$, (d) tetrazolyl, (e)—CH($OR^{17}$)—$CH_2OR^{18}$, (f) —$CH(OR^{17})$—$CH_2$—$CH_2OR^{18}$, (g)—$CH(OR^{17})$—$CH(OR^{18})$—$CH_2OR^{19}$, and (h)=N—$OR^{17}$.

$R^1$, $R^4$, $R^6$, $R^7$, $R^8$, $R^{17}$, $R^{18}$, and $R^{19}$ are independently selected at each occurrence from the group consisting of (a) hydrogen, (b) alkyl of one to six carbon atoms, (c) phenyl, (d) phenyl substituted one, two or three substituents selected from (d-1) halogen, (d-2) alkyl of one to six carbon atoms, (d-3) haloalkyl of one to six carbon atoms, (d-4) alkoxy of one to six carbon atoms, and (d-5)

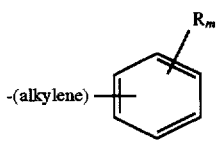

wherein the alkylene portion is of one to six carbon atoms, m is 0, 1, 2, or 3, and R, which may be the same or different at each occurrence, is selected from halogen, alkyl of one to six carbon atoms, haloalkyl of one to six carbon atoms, and alkoxy of one to six carbon atoms.

In those instances where M=OH, the compounds of the present invention are capable of forming base addition salts. In such instances, the term "pharmaceutically acceptable salts" refers to the relatively nontoxic inorganic and organic base addition salts of compounds of the present invention. These salts can be prepared in situ during the final isolation and purification of the compounds, or by separately reacting the purified carboxyl compound with a suitable base such as the hydroxide, carbonate, or bicarbonate of a pharmaceutically acceptable metal cation or with ammonia, or an organic primary, secondary, or tertiary amine of sufficient basicity to form a salt with the carboxyl functional group of the compounds of this invention.

Representative alkali or alkaline earth metal salts include sodium, lithium, potassium, calcium, magnesium, and the like. Representative organic amines useful for the formation of base addition salts include ethylamine, diethylamine, ethylenediamine, ethanolamine, diethanolamine, piperazine, and the like. (See, for example, S. M Berge, et al., *J. Pharmaceutical Sciences*, 1977, 66: 1–19, which is incorporated herein by reference).

Similarly, in those instances where the compounds of the present invention possess a heterocyclic ring moiety containing a basic nitrogen atom, the compounds are capable of forming acid addition salts. In such cases, the term "pharmaceutically acceptable salts" refers to the relatively non-toxic inorganic and organic acid addition salts of compounds of the present invention. These salts can be prepared in situ during the final isolation and purification of the compounds, or by separately reacting the purified compound in its free-base form with a suitable inorganic or organic acid and isolating the salt thus formed. Representative acid addition salts include acetate, adipate, alginate, ascorbate, aspartate, benzenesulfonate, benzoate, bisulfate, borate, butyrate, camphorate, camphersulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. (See, for example, S. M Berge, et al., *J. Pharmaceutical Sciences*, 1977, 66: 1–19, which is incorporated herein by reference). Said pharmaceutically acceptable acid and base addition salts are also contemplated as falling within the scope of the present invention.

The present invention also provides pharmaceutical compositions which comprise a therapeutically effective amount of compound of claim 1 in combination with a pharmaceutically acceptable carrier.

The invention further relates to a method of inhibiting prostaglandin biosynthesis in a host mammal in need of such treatment comprising administering to a mammal in need of such treatment a therapeutically effective amount of a compound of claim 1.

DETAILED DESCRIPTION

Definitions of Terms

As used throughout this specification and the appended claims, the following terms have the meanings specified.

The term alkyl refers to a monovalent group derived from a straight or branched chain saturated hydrocarbon by the removal of a single hydrogen atom. Alkyl groups are exemplified by methyl, ethyl, n- and iso-propyl, n-, sec-, iso- and tert-butyl, and the like.

The terms alkoxy and alkoxyl denote an alkyl group, as defined above, attached to the parent molecular moiety through an oxygen atom. Representative alkoxy groups include methoxy, ethoxy, propoxy, butoxy, and the like.

The terms alkenyl as used herein refer to monovalent straight or branched chain groups of 2 to 6 carbon atoms containing a carbon-carbon double bond, derived from an alkene by the removal of one hydrogen atom and include, but are not limited to groups such as ethenyl, 1-propenyl, 2-propenyl, 2-methyl-1-propenyl, 1-butenyl, 2-butenyl and the like.

The term alkylene denotes a divalent group derived from a straight or branched chain saturated hydrocarbon containing by the removal of two hydrogen atoms, for example —CH$_2$—, —CH$_2$CH$_2$—, —CH(CH3)CH$_2$—and the like.

The term aryl as used herein refers to a monovalent carbocyclic group containing one or more fused or non-fused phenyl rings and includes, for example, phenyl, 1- or 2-naphthyl, 1,2-dihydronaphthyl 1,2,3,4-tetrahydronaphthyl, and the like.

The term cycloalkyl as used herein refer to a monovalent saturated cyclic hydrocarbon group. Representative cycloalkyl groups include cyclopropyl, cyclobutyl, cyclopentyl, cyclohexyl, cycloheptyl, bicyclo[2.2.1]heptane and the like.

Cycloalkylene denotes a divalent radical derived from a cycloalkane by the removal of two hydrogen atoms.

The term haloalkyl denotes an alkyl group, as defined above, having one, two, or three halogen atoms attached thereto and is exemplified by such groups as chloromethyl, bromoethyl, trifluoromethyl, and the like.

The term hydroxyalkyl represents an alkyl group, as defined above, substituted by one to three hydroxyl groups with the proviso that no more than one hydroxy group may be attached to a single carbon atom of the alkyl group.

As used throughout this specification and the appended claims, the term "metabolically cleavable group" denotes a moiety which is readily cleaved in vivo from the compound bearing it, which compound after cleavage remains or becomes pharmacologically active. Metabolically cleavable groups form a class of groups reactive with the carboxyl group of the compounds of this invention (where M is —OH) well known to practitioners of the art. They include, but are not limited to such groups as alkanoyl (such as acetyl, propionyl, butyryl, and the like), unsubstituted and substituted aroyl (such as benzoyl and substituted benzoyl), alkoxycarbonyl (such as ethoxycarbonyl), trialkylsilyl (such as trimethyl- and triethysilyl), monoesters formed with dicarboxylic acids (such as succinyl), and the like. Because of the ease with which the metabolically cleavable groups of the compouns of this invention are cleaved in vivo, the compounds bearing such groups act as pro-drugs of other prostaglandin biosynthesis inhibitors. The compounds bearing the metabolically cleavable groups have the advantage that they may exhibit improved bioavailability as a result of enhanced solubility and/or rate of absorption conferred upon the parent compound by virtue of the presence of the metabolically cleavable group.

By "pharmaceutically acceptable cation" it is meant those base addition salts of the carboxy group —COOH which are, within the scope of sound medical judgement, suitable for use in contact with the tissues of humans and lower animals without undue toxicity, irritation, allergic response and the like, and are commensurate with a reasonable benefit/risk ratio. Pharmaceutically acceptable cations are well known in the art. For example, S. M Berge, et al. describe pharmaceutically acceptable salts in detail in *J. Pharmaceutical Sciences*, 1977, 66: 1–19. Representative pharmaceutically acceptable cations include alkali or alkaline earth metal cations such as sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like.

Asymmetric centers may exist in the compounds of the present invention. The present invention contemplates the various stereoisomers and mixtures thereof. Individual stereoisomers of compounds of the present invention are made by synthesis from starting materials containing the chiral centers or by preparation of mixtures of enantiomeric products followed by separation as, for example, by conversion to a mixture of diastereomers followed by separation by recrystallization or chromatographic techniques, or by direct separation of the optical enantiomers on chiral chromatographic columns. Starting compounds of particular stereochemistry are either commercially available or are made by the methods detailed below and resolved by techniques well known in the organic chemical arts.

Preferred Embodiments

Compounds contemplated as falling within the scope of the present invention include, but are not limited to
(4-chlorobenzoyl-5-methoxy-2-methylindol-3-yl) acetaldehyde-o-carboxymethyl oxime,
(4-chlorobenzoyl-5-methoxy-2-methylindol-3-yl) acetaldehyde-o-4-(2,2-dimethyldioxanylmethyloxycarbonylmethyl) oxime,
(4-chlorobenzoyl-5-methoxy-2-methylindol-3-yl) acetaldehyde-o-4-(2,2-dimethyldioxanylmethyloxycarbonylmethyl) oxime,
(4-chlorobenzoyl-5-methoxy-2-methylindol-3-yl) acetaldehyde-o-(2-carboxyethyl) oxime,
(4-chlorobenzoyl-5-methoxy-2-methylindol-3-yl) acetaldehyde-o-(2-hydroxyethyl) oxime,
(4-chlorobenzoyl-5-methoxy-2-methylindol-3-yl) acetaldehyde-o-(3-hydroxypropyl) oxime,
4-chlorobenzoyl-5-methoxy-2-methylindol-3-yl acetaldehyde-o-(2, 3-dihydroxpropyl) oxime,
4-chlorobenzoyl-5-methoxy-2-methylindol-3-yl acetaldehyde-o-(5-tetrazolylmethyl) oxime,
(4-chlorobenzoyl-5-methoxy-2-methylindol-3-yl) acetaldehyde-o-[(carboxy-2-hydroxyethylamide) methyl] oxime,
(4-chlorobenzoyl-5-methoxy-2-methylindol-3-yl) acetaldehyde-o-(acetohydroxamic acid) oxime,
(4-chlorophenylmethyl-5-methoxy-2-methylindol-3-yl) acetaldehyde-o-carboxymethyl oxime,
1-[1-(4-chlorophenylmethyl-5-methoxy-2-methylindol-3-yl)] propan-2-one-o-carboxymethyl oxime,
(2-pyridylmethyl-5-methoxy-2-methylindol-3-yl) acetaldehyde-o-carboxymethyl oxime,
(3-pyridylmethyl-5-methoxy-2-methylindol-3-yl) acetaldehyde-o-carboxymethyl oxime,
(4-pyridylmethyl-5-methoxy-2-methylindol-3-yl) acetaldehyde-o-carboxymethyl oxime,
(1-t-butoxycarbonyl-5-(quinol-2-ylmethoxy)-2-methylindol-3-yl) acetaldehyde-o-carboxymethyl oxime,
[1-(4-chlorophenylmethyl)-5-(quinol-2-ylmethoxy)-2-methylindol-3-yl] acetaldehyde-o-carboxymethyl oxime,
[4-chorophenylmethyl-5-(benzothiazol-2-ylmethoxy)-2-methylindol-3-yl] acetaldehyde-o-carboxymethyl oxime,
[4-chorophenylmethyl-5-(thiazol-2-ylmethoxy)-2-methylindol-3-yl] acetaldehyde-o-carboxymethyl oxime,
[4-pyridylmethyl-5-(thiazol-2-ylmethoxy)-2-methylindol-3-yl] acetaldehyde-o-carboxymethyl oxime,
[5-fluoro-2-methyl-1-[(4-methylsulfinyl)phenylmethyl]-1H-inden-3-yl] acetaldehyde-o-carboxymethyl oxime,
[5-fluoro-2-methyl-1-[(4-methylsulfinyl)phenylmethyl]-1H-inden-3-yl] acetaldehyde-o-(2-carboxyethyl) oxime,
[5-fluoro-2-methyl-1-[(4-methylsulfinyl)phenylmethyl]-1H-inden-3-yl] acetaldehyde-o-(2-hydroxypropyl) oxime,
[5-fluoro-2-methyl-1-[(4-methylsulfinyl)phenylmethyl]-1H-inden-3-yl] acetaldehyde-o-(3-hydroxypropyl) oxime,
[5-fluoro-2-methyl-1-[(4-methylsulfinyl)phenylmethyl]-1H-inden-3-yl] acetaldehyde-o-(2,3-dihydroxypropyl) oxime, and
[5-fluoro-2-methyl-1-[(4-methylsulfinyl)phenylmethyl]-1H-inden-3-yl] acetaldehyde-o-(5-tetrazolylmethyl) oxime.

In a preferred embodiment, the compounds of the present invention have the structure above wherein A is alkylene of one to six carbon atoms, Z is selected from the group consisting of (a)—COM wherein M is selected from the group consisting of (a-1)—$OR^{10}$ wherein $R^{10}$ is selected from the group consisting of a pharmaceutically acceptable cation, hydrogen, (a-2) —$O(CH_2)_w$—$CH(OR^{12})$—$CH_2OR^{13}$ wherein w is 1, 2, or 3, and $R^{12}$ and $R^{13}$ are independently selected from hydrogen and alkyl of one to six carbon atoms, or $R^{12}$ and $R^{13}$ together with the oxygen atoms to which they are attached define a 5- or 6-membered heterocyclic ring which may be optionally substituted with alkyl of one to six carbon atoms, haloalkyl of one to six carbon atoms, and alkoxy of one to six carbon atoms, and (a-3)-$NR^{15}R^{16}$ wherein $R^{15}$ and $R^{16}$ are independently selected from hydrogen, alkyl of one to six carbon atoms, hydroxyalkyl of one to six carbon atoms, and hydroxy, (b) tetrazolyl, (c)—$CH(OR^{17})$—$CH_2OR^{18}$, (d)—$CH(OR^{17})$—$CH_2$—$CH_2OR^{18}$, and (e)—$CH(OR^{17})$—$CH(OR^{18})$—$CH_2OR^{19}$, wherein $R^{17}$, $R^{18}$, and $R^{19}$ are independently selected from hydrogen and alkyl of one to six carbon atoms; and $Y_n$, X, $R^1$, $R^2$, $R^3$, and $R^4$ are defined above.

More preferred compounds have the structure

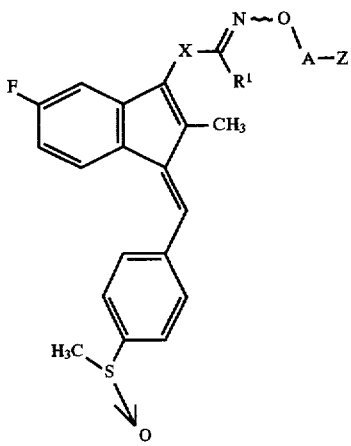

wherein X, R¹, A, and Z are defined immediately above.

Still more preferred compounds of the present invention have the structure immediately above wherein Z is selected from

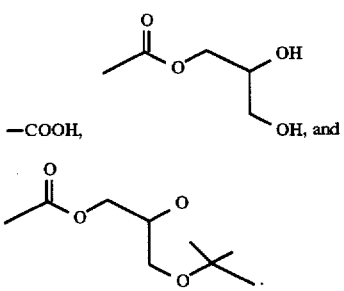

Still yet more preferred compounds of the present invention have the structure

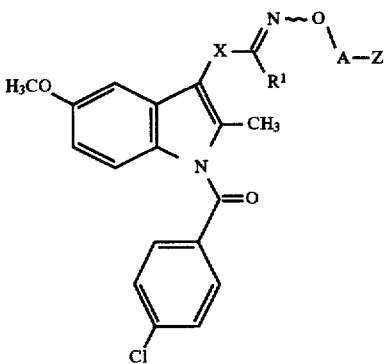

wherein A is alkylene of one to six carbon atoms, Z is selected from the group consisting of (a)—COM wherein M is selected from the group consisting of (a-1)—OR$^{10}$ wherein R$^{10}$ is selected from the group consisting of a pharmaceutically acceptable cation, hydrogen, (a-2)—O(CH$_2$)$_w$—CH(OR$^{12}$)—CH$_2$OR$^{13}$ wherein w is 1, 2, or 3, and R$^{12}$ and R$^{13}$ are independently selected from hydrogen and alkyl of one to six carbon atoms, or R$^{12}$ and R$^{13}$ together with the oxygen atoms to which they are attached define a 5- or 6-membered heterocyclic ring which may be optionally substituted with alkyl of one to six carbon atoms, haloalkyl of one to six carbon atoms, and alkoxy of one to six carbon atoms, and (a-3)—NR$^{15}$R$^{16}$ wherein R$^{15}$ and R$^{16}$ are independently selected from hydrogen, alkyl of one to six carbon atoms, hydroxyalkyl of one to six carbon atoms, and hydroxy, (b) tetrazolyl, (c)—CH(OR$^{17}$)—CH$_2$OR$^{18}$, (d)—CH(OR$^{17}$)—CH$_2$—CH$_2$OR$^{18}$, and (e) —CH(OR$^{17}$)—CH(OR$^{18}$)—CH$_2$OR$^{19}$, wherein R$^{17}$, R$^{18}$, and R$^{19}$ are independently selected from hydrogen and alkyl of one to six carbon atoms.

The most preferred compounds of the present invention have the structure immediately above wherein Z is selected from

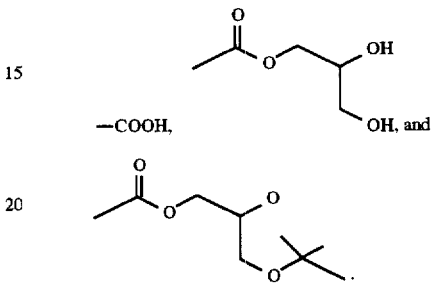

Compounds representative of the most preferred embodiment include, but are not limited to (4-chlorobenzoyl-5-methoxy-2-methylindol-3-yl) acetaldehyde-o-carboxymethyl oxime, (4-chlorobenzoyl-5-methoxy-2-methylindol-3-yl) acetaldehyde-o-4-(2,2-dimethyldioxanylmethyloxycarbonylmethyl) oxime, and (4-chlorobenzoyl-5-methoxy-2-methylindol-3-yl) acetaldehyde-o-4-(2,2-dimethyldioxanylmethyloxycarbonylmethyl) oxime.

PROSTAGLANDIN INHIBITION DETERMINATION

Inhibition of prostaglandin biosynthesis was evaluated in recombinant human PGHS-1 and PGHS-2 enzyme assays. Representative compounds dissolved in DMSO (3.3% v/v) were preincubated with microsomes from recombinant human PGHS-1 or PGHS-2 expressed in the baculovirus/Sf9 cell system (Gierse, J. K., Hauser, S. D., Creely, D. P., Koboldt, C., Rangwala, S., H., Isakson, P. C., and Seibert, K. Expression and selective inhibition of the constituitive and inducible forms of cyclooxygenase Biochem J. 1995, 305: 479.), together with the cofactors phenol (2 mM) and hematin (1 µM) for 60 minutes prior to the addition of 10 µM arachidonic acid. The reaction was allowed to run for 2.5 minutes at room temperature prior to quenching with HCl and neutralization with NaOH. PGE$_2$ production in the presence and absence of the drug was determined by EIA analysis. The EIA was conducted in 96 well microtiter plates (Nunc Roskilde, Denmark) and optical density measured using a microplate reader (Vmax, Molecular Devices Corp., Menlo Park, Calif.). EIA reagents for prostaglandin determination were purchased from Perseptive Diagnostics, Cambridge, Mass. PGE$_2$ levels were measured against standards prepared in the same milieu. The immunoassays were conducted as recommended by the manufacturer.

The compounds of this invention inhibit prostaglandin biosynthesis as shown by the data for the representative example 1 in Table 1.

TABLE 1

In Vitro Inhibitory Potencies Against Human Recombinant PGHS-1 and PGHS-2

| Example | PGHS-1 IC$_{50}$ (µM) | PGHS-2 IC$_{50}$ (µM) |
|---|---|---|
| 1 | — | 0.73 |
| 2 | 0.09 | 0.003 |
| 3 | 41% @ 1 µM | 70% @ 0.1 µM |

Pharmaceutical Compositions

The present invention also provides pharmaceutical compositions which comprise compounds of the present invention formulated together with one or more non-toxic pharmaceutically acceptable carriers. The pharmaceutical compositions may be specially formulated for oral administration in solid or liquid form, for parenteral injection, or for rectal administration.

The pharmaceutical compositions of this invention can be administered to humans and other animals orally, rectally, parenterally, intracisternally, intravaginally, intraperitoneally, topically (as by powders, ointments, or drops), bucally, or as an oral or nasal spray. The term "parenteral" administration as used herein refers to modes of administration which include intravenous, intramuscular, intraperitoneal, intrasternal, subcutaneous and intraarticular injection and infusion.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as preservative, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption such as aluminum monostearate and gelatin.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides) Depot injectable formulations are also prepared by entrapping the drug in liposomes or microemulsions which are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic.

Methods to form liposomes are known in the art. See, for example, Prescott, Ed., *Methods in Cell Biology*, Volume XIV, Academic Press, New York, N. Y. (1976), p. 33 et seq.

Dosage forms for topical administration of a compound of this invention include powders, sprays, ointments and inhalants. The active compound is mixed under sterile conditions with a pharmaceutically acceptable carrier and any needed preservatives, buffers, or propellants which may be required. Opthalmic formulations, eye ointments, powders and solutions are also contemplated as being within the scope of this invention.

Actual dosage levels of active ingredients in the pharmaceutical compositions of this invention may be varied so as to obtain an amount of the active compound(s) that is effective to achieve the desired therapeutic response for a particular patient, compositions, and mode of administration. The selected dosage level will depend upon the activity of the particular compound, the route of administration, the severity of the condition being treated, and the condition and prior medical history of the patient being treated. However, it is within the skill of the art to start doses of the compound at levels lower than required for to achieve the desired therapeutic effect and to gradually increase the dosage until the desired effect is achieved.

Generally dosage levels of about 1 to about 50, more preferably of about 5 to about 20 mg of active compound per kilogram of body weight per day are administered orally to a mammalian patient. If desired, the effective daily dose may be divided into multiple doses for purposes of administration, e.g. two to four separate doses per day.

Preparation of Compounds of this Invention

The compounds of this invention can be prepared by representative methods described as follows. Indomethacin, sulindac, and their synthetic analogs serve as starting material for the preparation of the compounds of this invention. See Shen, T. Y. and Winter, C. A., *Chemical and Biological Studies on Indomethacin, Sulindac and their Analogs*, Advances in Drug Research, 12, Simmonds, A. B., Ed., Academic Press, New York, 89 (1977); and Gund, P.; Shen, T. Y. A *Model for the Prostaglandin Synthetase Cyclooxygenase Site and its Inhibition by Antiinflammatory Arylacetic Acids*, J. Med. Chem., 20, 1146, (1977) for the preparation of the synthetic anaglogs used as starting materials for the compounds of this invention.

A general synthetic route to the compounds of this invention is outlined in Scheme 1. Selective reduction of the carboxylate group of indomethacin or sulindac derivatives by known methods such as diisobutylaluminum hydride provides the corresponding aldehyde intermediate III. Alternatively, the requisite aldehyde intermediate can be prepared by reduction of the carboxylate group to the corresponding hydroxy intermediate II using, for example, lithium aluminum hydride or borane.THF, followed by oxidation to the desired aldehyde intermediate III by standard methods such as the Swern oxidation (Swern, et al., *J. Org. Chem.*, 1978, 43, 2480). Reaction of the aldehyde intermediate III with hydroxylamine IV provides the desired oxime derivatives in which $R^1$ is H.

Scheme 1

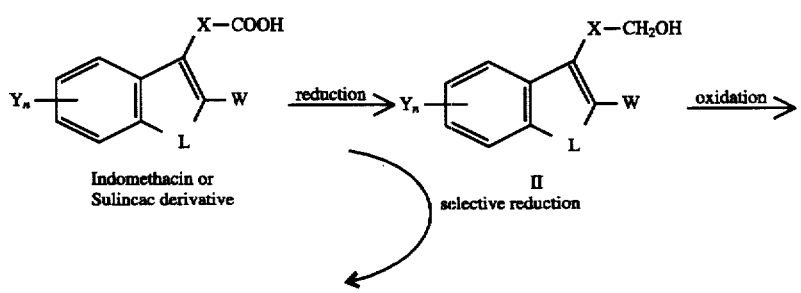

-continued
Scheme 1

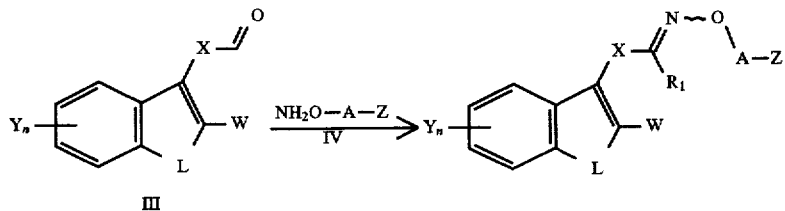

Formula 1 R₁ = H, W = CH₃, X = CH₂
L = NR², C = CR³R⁴

Compounds of the present invention in which $R^1$ is other than hydrogen are prepared as outlined in Scheme 2. Reaction of the aldehyde intermediate III with a nucleophilic species derived from $R^1$ provides the hydroxy intermediate V. Especially preferred nucleophilic species are organolithium reagents of formula $R^1Li$ and Grignard reagents of formula $R^1MgX$ wherein X is Br or Cl. The desired compounds are then prepared by oxidation of the hydroxy intermediate V to the corresponding ketone VI and subsequent reaction of VI with hydroxylamine derivative IV as described in Scheme 1 above.

Scheme 2

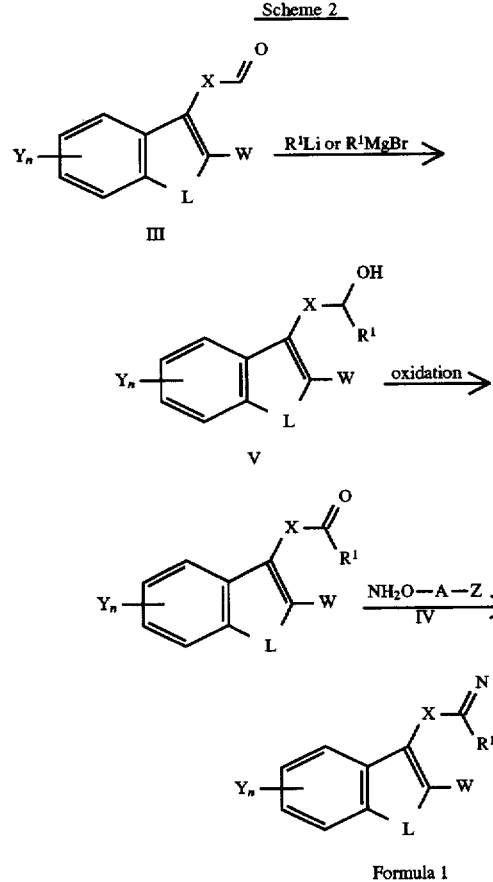

Formula 1

The hydroxylamine intermediate NH₂O—A—Z is prepared reaction of the alcohol HO—A—Z with N-hydroxyphthalimide, triphenylphosphine, and diethyl- or diisopropylazodicarboxylate to form the N-phthaloylhydroxlamine derivative, which is converted to the hydroxylamine IV by reaction with hydrazine as shown is scheme 3.

Scheme 3

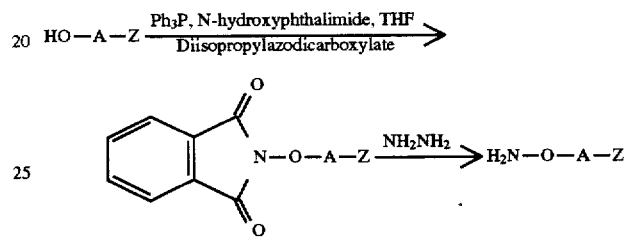

The foregoing may be better understood by reference to the following examples which are provided for illustration and not intended to limit the scope of the inventive concept. The compounds of this invention consist of E and Z isomers of the oxime function and R and S enantiomers when there is an asymmetric carbon center. The individual or mixtures of isomers and/or enantiomers are considered as part of this invention.

EXAMPLE 1

Preparation of (4-chlorobenzoyl-5-methoxy-2-methylindol-3-yl) acetaldehyde-o-carboxymethyl oxime

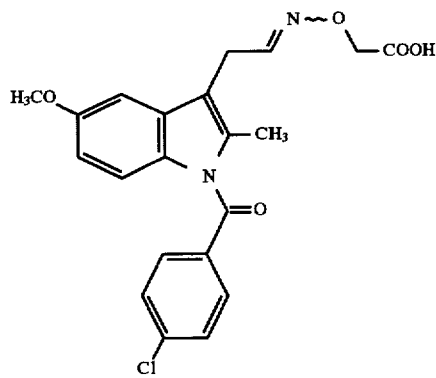

Step 1: 2-(4-chlorobenzoyl-5-methoxy-2-methylindol-3-yl) ethanol.

To a magnetically stirred–20° C. solution of indomethacin (7.5 g, 21 mmol) in dry THF (42 mL) was added dropwise BH₃:THF (1.0 M in THF, 22 mL), and the mixture was stirred at 0° C. for 2 hours. Crushed ice was added and the mixture was poured into 10% aqueous citric acid (200 mL) and extracted with ethyl acetate (3×100 mL). The combined organic layers were washed with water and brine, dried over MgSO₄, filtered, and evaporated in vacuo. Purification by chromatography (silica gel, 10:3 hexane/ethyl acetate) afforded 6.95 g (96.7%) of 2-(4-chlorobenzoyl-5-methoxy-2-methylindol-3-yl) ethanol.

Step 2: (4-chlorobenzoyl-5-methoxy-2-methylindol-3-yl) acetaldehyde.

To a mixture in dry DMSO (11.6 mL) of 2-(4-chlorobenzoyl-5-methoxy-2-methylindol-3-yl) ethanol (2.0 g, 5.8 mmol), prepared as in step 1, and dicyclohexylcarbodiimide (DCC) (1.6 g, 7.8 mmol) was added 1.0 M $H_3PO_4$ in DMSO (1.0 mL) and the reaction mixture was stirred at room temperature for 48 hours. Diethyl ether (100 mL) was added and the solid dicyclohexylurea byproduct was removed by filtration. The filtrate was washed with water, dried over $MgSO_4$, filtered, and evaporated in vacuo. The crude product was triturated with hexane/ether to give 1.9 g (95%) of (4-chlorobenzoyl-5-methoxy-2-methylindol-3-yl) acetaldehyde.

Step 3: (4-chlorobenzoyl-5-methoxy-2-methylindol-3-yl) acetaldehyde-o-carboxymethyl oxime.

A mixture in ethanol (10 mL) of (4-chlorobenzoyl-5-methoxy-2-methylindol-3-yl) acetaldehyde (0.46 g, 1.35 mmol), prepared as in step 2, o-carboxymethyl hydroxylamine hemihydrochloride (0.325 g, 1.49 mmol), and pyridine (3.5 mL) was stirred at reflux for 18 hours. After cooling, the reaction mixture was concentrated and acidified to pH 2 with 10% aqueous citric acid. The mixture was extracted with ethyl acetate (4×100 mL), and the combined organic layers were washed with water and brine, dried over $MgSO_4$, filtered, and evaporated in vacuo. Purification by chromatography (silica gel, 95:5:0.5 $CH_2Cl_2$, $CH_3OH$, trifluoroacetic acid) and crystallization from diethyl ether gave 360 mg (64%) of a 1:1 mixture of E and Z isomers of 4-chlorobenzoyl-5-methoxy-2-methylindol-3-ylacetaldehyde-o-carboxymethyl oxime. mp 136–139° C.; $^1H$ NMR (300 MHz, DMSO-$d_6$) δ2.23(s, 3H), 3.58 (d J =6.9 Hz, 1H), 3.74 (d, J=6.9 Hz, 1H), 3.77 (s, 3H), 4.49 (s, 1H), 4.65 (s, 1H), 6.72 (m, 1H), 6.88 (t, J=6.0 Hz, 0.5H), 6.94 (d, J =9 Hz, 0.5H), 6.97 (d, J=9 Hz, 0.5H), 6.99 (m,1H), 7.54 (t, J=6.0 Hz, 0.5H), 7.67 (m, 4H), 12.76 (s, 1H); MS (DCI-NH3) m/z 415 (M+H)$^+$, 432 (M+NH$_4$)$^+$. Anal. Calcd for $C_{21}H_{19}ClN_2O_5$: C, 60.80; H, 4.62; N, 6.75. Found: C, 60.89; H, 4.40; N, 6.68.

EXAMPLE 2

Preparation of (4-chlorobenzoyl-5-methoxy-2-methylindol-3-yl) acetaldehyde-o-4-(2,2-dimethyldioxanylmethyloxycarbonylmethyl) oxime

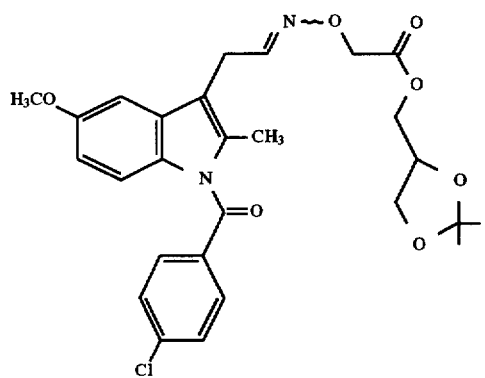

To a solution in 3:1 THF:$CH_3CN$ of 4-chlorobenzoyl-5-methoxy-2-methylindol-3-ylacetaldehyde-o-carboxymethyl oxime (1.14 mmol), prepared as in Example 1, was added 2,2-dimethyl-3-dioxolane-4-methanol (1.7 mmol), 4-dimethylaminopyridine (1.7 mmol), and 1-(3-dimethylaminopropyl)-3-ethylcarbodiimide hydrochloride (EDCI, 1.7 mmol) and the mixture was stirred at room temperature for 18 hours. The reaction mixture was poured into water and extracted with ethyl acetate. The ethyl acetate extracts were washed with water and brine, dried over $MgSO_4$, filtered, and concentrated in vacuo. The residue was purified by column chromatography on silica gel (20% ethyl acetate/hexanes) to give 4-chlorobenzoyl-5-methoxy-2-methylindol-3-yl) acetaldehyde-o-4-(2,2-dimethyldioxanylmethyloxycarbonylmethyl) oxime (0.135 g, 22%) as an oil. $^1H$ NMR (300 MHz, DMSO-$d_6$) δ1.24–1.35 (ms, 6H), 2.24 (m, 3H), 3.55–3.70 (m, 2H), 3.78–3.80 (m, 4H), 3.93–4.28 (m, 4H), 4.63 (s, 1H), 4.79 (s, 2H), 6.73 (m, 1H), 6.90–6.98 (m, 2H), 7.09 (m, 1H), 7.55–7.72 (m, 4H); MS(DCI-NH$_3$) m/z 546 (M+NH$_4$)$^+$, 529 (M+H)$^+$.

EXAMPLE 3

Preparation of (4-chlorobenzoyl-5-methoxy-2-methylindol-3-yl) acetaldehyde-o-4-(2,3-dihydroxypropyloxycarbonylmethyl) oxime

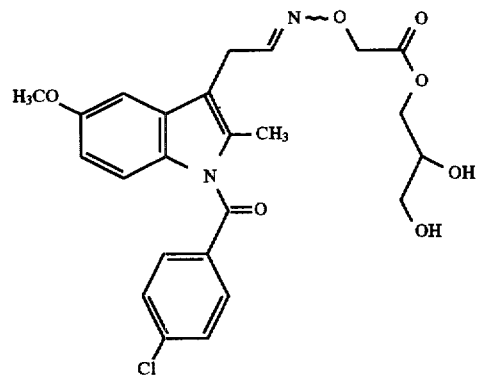

A mixture of 4-chlorobenzoyl-5-methoxy-2-methylindol-3-yl) acetaldehyde-o-4-(2,2-dimethyldioxanylmethyloxycarbonylmethyl) oxime (0.18 mmol), prepared as in Example 2, in 85% ethanol (4 mL) and $H_2SO^4$(0.19 mL, 2N) was stirred for 4 hours at 80° C. The mixture was poured into water and extracted with ethyl acetate. The ethyl acetate extracts were washed with water and brine, dried over $MgSO_4$, filtered, and concentrated in vacuo. The residue was purified by column chromatography on silica gel (hexanes) to give (4-chlorobenzoyl-5-methoxy-2-methylindol-3-yl) acetaldehyde-o-4-(2,3-dihydroxypropyloxycarbonylmethyl) oxime (0.017 g, 18%). $^1H$ NMR (300 MHz, DMSO-$d_6$) δ2.02 (m, 1H), 2.38 (2s, 3H), 2.47 (m,1H), 3.54–4.00 (m, 7H), 3.86 (s, 3H), 4.62 (s, 1H), 4.78 (s 1H), 6.68 (m, 1H), 6.78–6.92 (m, 2H), 6.96 (d, 1H), 7.48 (m, 2H), 7.68 (m, 2H); MS (DCI-NH$_3$) m/z 506 (M+NH$_4$)$^+$, 489 (M+H)$^+$.

EXAMPLE 4

Preparation of (4-chlorobenzoyl-5-methoxy-2-methylindol-3-yl) acetaldehyde-o-(2-carboxyethyl) oxime

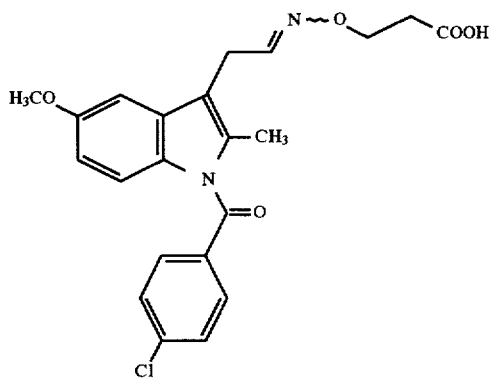

The title compound is prepared according to the method of Example 1, step 4, except substituting o-2-carboxyethyl hydroxylamine hydrochloride for o-carboxymethyl hydroxylamine hemihydrochloride.

EXAMPLE 5
Preparation of (4-chlorobenzoyl-5-methoxy-2-methylindol-3-yl) acetaldehyde-o-(2-hydroxyethyl) oxime

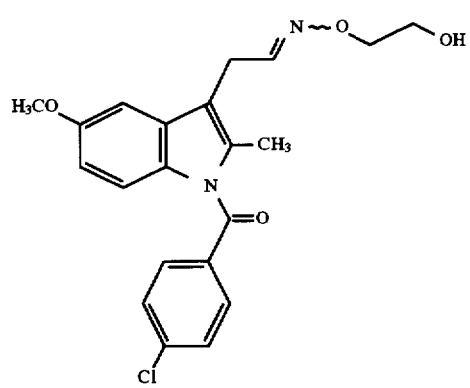

The title compound is prepared by reduction of 4-chlorobenzoyl-5-methoxy-2-methylindol-3-ylacetaldehyde-o-carboxymethyl oxime, prepared as in Example 1, with diborane: THF.

EXAMPLE 6
Preparation of (4-chlorobenzoyl-5-methoxy-2-methylindol-3-yl) acetaldehyde-o-(3-hydroxypropyl) oxime

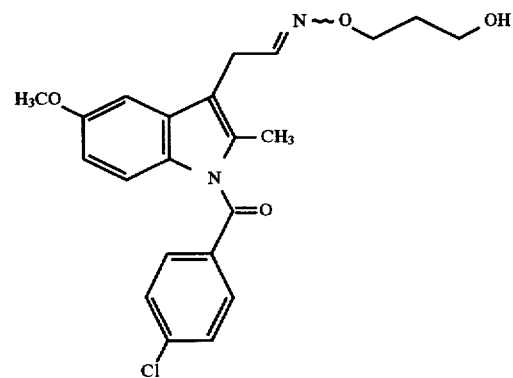

The title compound is prepared by reduction of the product of (4-chlorobenzoyl-5-methoxy-2-methylindol-3-yl) acetaldehyde-o-(2-carboxyethyl) oxime, prepared as in Example 3, with diborane: THF.

EXAMPLE 7

Preparation of 4-chlorobenzoyl-5-methoxy-2-methylindol-3-yl acetaldehyde-o-(2,3-dihydroxpropyl) oxime

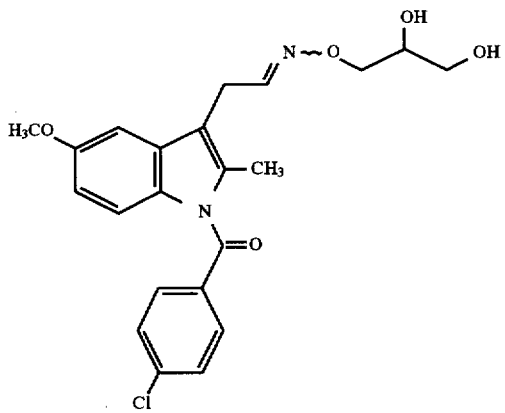

The title compound is prepared according to the method of Example 1, step 3, except substituting o-(2,3 dihydroxypropyl) hydroxylamine for o-carboxymethyl hydroxylamine hemihydrochloride.

EXAMPLE 8

Preparation of 4-chlorobenzoyl-5-methoxy-2-methylindol-3-yl acetaldehyde-o-(5-tetrazolylmethyl) oxime

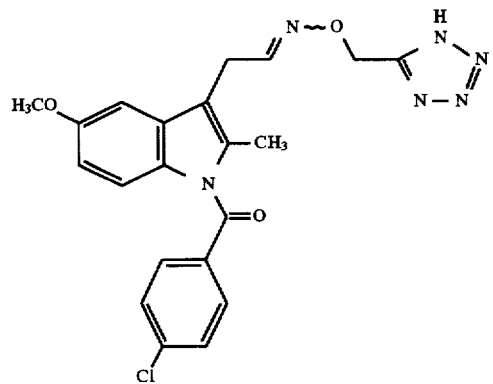

The title compound is prepared according to the method of Example 1, step 4, except substituting o-(5-tetrazolylmethyl) hydroxylamine for o-carboxymethyl hydroxylamine hemihydrochloride.

EXAMPLE 9

Preparation of (4-chlorobenzoyl-5-methoxy-2-methylindol-3-yl) acetaldehyde-o-[(carboxy-2-hydroxyethylamide) methyl] oxime

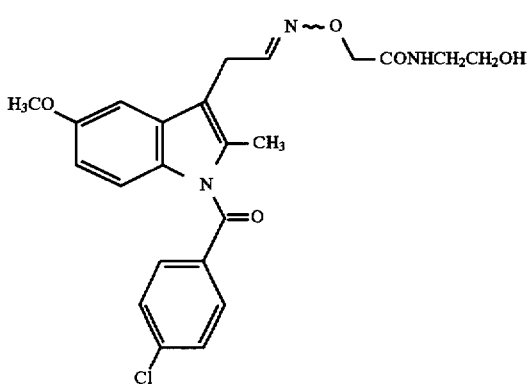

The title compound is prepared by the reaction of 4-chlorobenzoyl-5-methoxy-2-methylindol-3-ylacetaldehyde-o-carboxymethyl oxime, prepared as in Example 1, with oxalyl chloride followed by the addition of ethanolamine.

EXAMPLE 10

Preparation of (4-chlorobenzoyl-5-methoxy-2-methylindol-3-yl) acetaldehyde-o-(acetohydroxamic acid) oxime

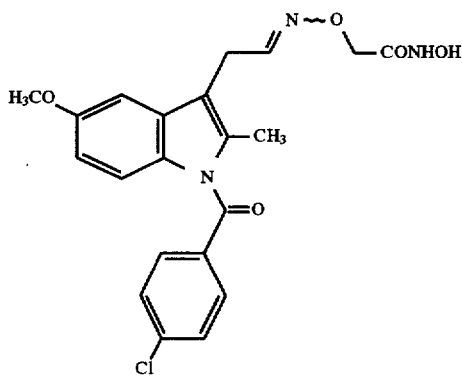

The title compound is prepared by the reaction of 4-chlorobenzoyl-5-methoxy-2-methylindol-3-ylacetaldehyde-o-carboxymethyl oxime, prepared as in Example 1, with oxalyl chloride followed by the addition of hydroxylamine.

EXAMPLE 11

Preparation of (4-chlorophenylmethyl-5-methoxy-2-methylindol-3-yl) acetaldehyde-o-carboxymethyl oxime

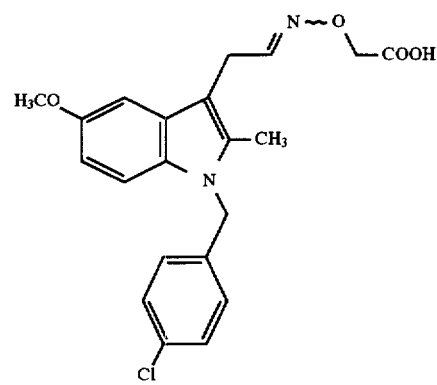

Step 1: (4-chlorophenylmethyl-5-methoxy-2-methylindol-3-yl)indoleacetic acid 4-chlorophenylmethyl ester.

The desired compound is prepared by reaction of commercially available 5-methoxy-2-methyl-3-indoleacetic acid with two equivalents of 4-chlorophenylmethylchloride and an appropriate base such as sodium hydride.

Step 2: 2-(4-chlorophenylmethyl-5-methoxy-2-methylindol-3-yl)ethanol.

The desired compound is prepared by reduction of (4-chlorophenylmethyl-5-methoxy-2-methylindol-3-yl) indoleacetic acid 4-chlorophenylmethyl ester, prepared as in step 1, with $LiAlH_4$.

Step 3: (4-chlorophenylmethyl-5-methoxy-2-methylindol-3-yl) acetaldehyde-o-carboxymethyl oxime.

The desired compound is prepared according to the method of Example 1, steps 2–3, except substituting 2-(4-chlorophenylmethyl-5-methoxy-2-methylindol-3-yl) ethanol, prepared as in step 2, for 2-(4-chlorobenzoyl-5-methoxy-2-methylindol-3-yl) ethanol.

EXAMPLE 12

Preparation of 1-[1-(4-chlorophenylmethyl-5-methoxy-2-methylindol-3-yl] propan-2-one-o-carboxymethyl oxime

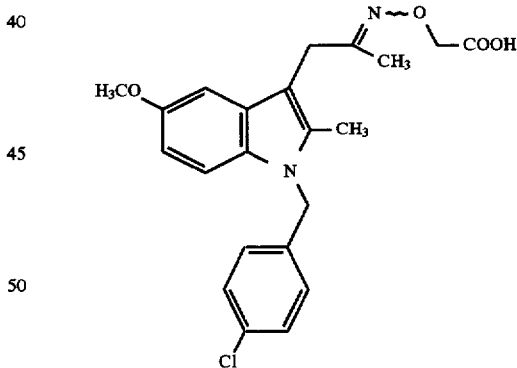

Step 1: 1-[1-(4-chlorophenylmethyl-5-methoxy-2-methylindol-3-yl)]propan-2-ol.

The title compound is prepared by the reaction of 4-chlorophenylmethyl-5-methoxy-2-methylindol-3-yl acetaldehyde, prepared as in Example 1, steps 1–3, with $CH_3MgBr$.

Step 2: 1-[1-(4-chlorophenylmethyl-5-methoxy-2-methylindol-3-yl] propan-2-one-o-carboxymethyl oxime.

The desired compound is prepared according to the method of Example 1, steps 2–3, except substituting 1-[1-

(4-chlorophenylmethyl-5-methoxy-2-methylindol-3-yl)] propan-2-ol, prepared as in step 1, for 2-(4-chlorobenzoyl-5-methoxy-2-methylindol-3-yl) ethanol.

EXAMPLE 13
Preparation of (2-pyridylmethyl-5-methoxy-2-methylindol-3-yl) acetaldehyde-o-carboxymethyl oxime

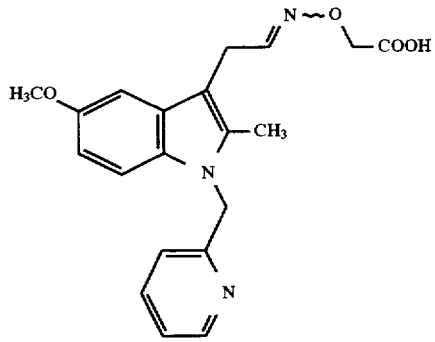

The desired compound is prepared according to the method of Example 11, except substituting 2-pyridylmethylchloride for 4-chlorophenylmethyl chloride.

EXAMPLE 14
Preparation of (3-pyridylmethyl-5-methoxy-2-methylindol-3-yl) acetaldehyde-o-carboxymethyl oxime

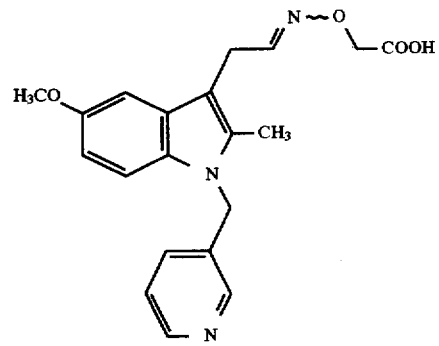

The desired compound is prepared according to the method of Example 13, except substituting 3-pyridylmethyl chloride for 2-pyridylmethyl chloride.

EXAMPLE 15
Preparation of (4-pyridylmethyl-5-methoxy-2-methylindol-3-yl) acetaldehyde-o-carboxymethyl oxime

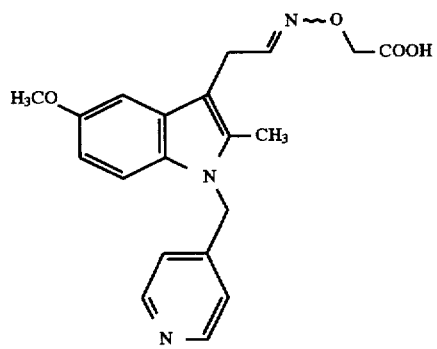

The desired compound is prepared according to the method of Example 13, except substituting 4-pyridylmethyl chloride for 2-pyridylmethyl chloride.

EXAMPLE 16
Preparation of (1-t-butoxycarbonyl-5-(quinol-2-ylmethoxy)-2-methylindol-3-yl) acetaldehyde-o-carboxymethyl oxime

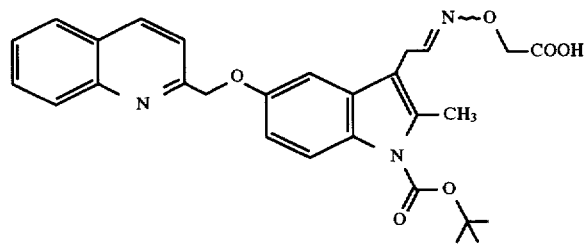

Step 1: 1-t-butoxycarbonyl-5-hydroxy-2-methylindol-3-yl acetic acid.

The title compound is prepared from 1-t-butoxycarbonyl-5-methoxy-2-methylindol-3-yl acetic acid by treatment with $BBr_3$.

Step 2: 1-t=butoxycarbonyl-5-(quinol-2-ylmethoxy)-2-methylindol-3-yl) acetic acid quinol-2-yl ester.

The desired compound is prepared by reaction of 1-t-butoxycarbonyl-5-hydroxy-2-methylindol-3-yl acetic acid, prepared as in step 1, with two equivalents of 2-quinolylmethylchloride in the presence of a suitable base such as $K_2CO_3$.

Step 3: 1-t=butoxycarbonyl-5-(quinol-2-ylmethoxy)-2-methylindol-3-yl) acetic acid.

The desired compound is prepared by saponification of 1-t=butoxycarbonyl-5-(quinol-2-ylmethoxy)-2-methylindol-3-yl) acetic acid quinol-2-yl ester, prepared as in step 2, using.

Step 4: (1-t-butoxycarbonyl-5-(quinol-2-ylmethoxy)-2-methylindol-3-yl) acetaldehyde-o-carboxymethyl oxime.

The desired compound is prepared according to the method of Example 1, except substituting 1-t-butoxycarbonyl-5-(quinol-2-ylmethoxy)-2-methylindol-3-yl) acetic acid, prepared as in step 3, for indomethacin.

EXAMPLE 17
Preparation of [1-(4-chlorophenylmethyl)-5-(quinol-2-ylmethoxy)-2-methylindol-3-yl] acetaldehyde-o-carboxymethyl oxime

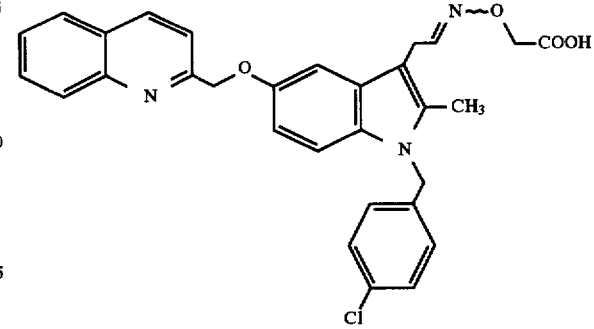

Step 1: 5-(quinol-2-ylmethoxy)-2-methylindol-3-ylacetaldehyde-o-carboxymethyl oxime.

The title compound is prepared from 1-t-butoxycarbonyl-5-(quinol-2-ylmethoxy)-2-methylindol-3-ylacetaldehyde-o-carboxymethyl oxime, prepared as in example 16, by treatment with trifluoroacetic acid to cleave the t-BOC group.

Step 2: 1-(4-chlorophenylmethyl)-5-(quinol-2-ylmethoxy)-2-methylindol-3-ylacetaldehyde-o-(acetic acid 4-chlorophenylmethyl ester) oxime.

The desired compound is prepared by reaction of 5-(quinol-2-ylmethoxy)-2-methylindol-3-ylacetaldehyde-o-carboxymethyl oxime, prepared as in step 1, with two equivalents of 4-chlorophenylmethylchloride in the presence of a suitable base such as $K_2CO_3$ or NaH.

Step 3: 1-(4-chlorophenylmethyl)-5-(quinol-2-ylmethoxy)-2-methylindol-3-yl] acetaldehyde-o-carboxymethyl oxime.

The desired compound is prepared by saponification of 1-(4-chlorophenylmethyl)-5-(quinol-2-ylmethoxy)-2-methylindol-3-ylacetaldehyde-o-(acetic acid 4-chlorophenylmethyl ester) oxime, prepared as in step 2, with.

EXAMPLE 18

Preparation of [4-chorophenylmethyl-5-(benzothiazol-2-ylmethoxy)-2-methylindol-3-yl] acetaldehyde-o-carboxymethyl oxime

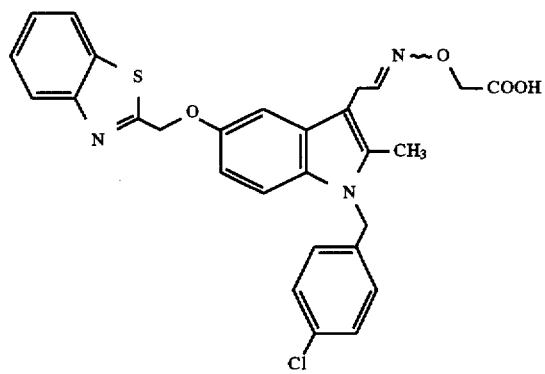

Step 1: (1-t-butoxycarbonyl-5-(benzothiazol-2-ylmethoxy)-2-methylindol-3-yl) acetaldehyde-o-carboxymethyl oxime.

The desired compound is prepared according to the method of Example 16, except substituting benzothiazol-2-ylmethyl chloride for 2-quinolylmethylchloride.

Step 2: [4-chorophenylmethyl-5-(benzothiazol-2-ylmethoxy)-2-methylindol-3-yl] acetaldehyde-o-carboxymethyl oxime.

The desired compound is prepared according to the method of Example 17, except substituting (1-t-butoxycarbonyl-5-(benzothiazol-2-ylmethoxy)-2-methylindol-3-yl) acetaldehyde-o-carboxymethyl oxime, prepared as in step 1, for 1-t-butoxycarbonyl-5-(quinol-2-ylmethoxy)-2-methylindol-3-ylacetaldehyde-o-carboxymethyl oxime.

EXAMPLE 19

Preparation of [4-chorophenylmethyl-5-(thiazol-2-ylmethoxy)-2-methylindol-3-yl] acetaldehyde-o-carboxymethyl oxime

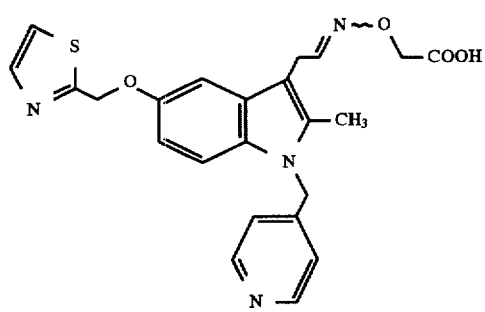

The desired compound is prepared according to the method of Example 18, except substituting thiazol-2ylmethyl chloride for of benzothiazol-2-ylmethyl chloride.

EXAMPLE 20

Preparation of [4-pyridylmethyl-5-(thiazol-2-ylmethoxy)-2-methylindol-3-yl] acetaldehyde-o-carboxymethyl oxime The title compound is prepared according to the method of Example 19, except substituting 4-pyridylmethylchloride for 4-chlorophenylmethylchloride.

EXAMPLE 21

Preparation of [5-fluoro-2-methyl- 1-[(4-methylsulfinyl)phenylmethyl]- 1H-inden-3-yl] acetaldehyde-o-carboxymethyl oxime

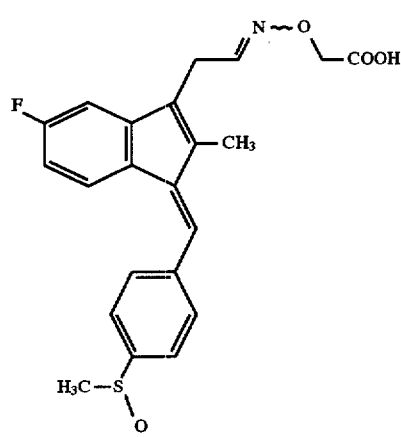

The title compound is prepared by the method of Example 1 using sulindac instead of indomethacin.

EXAMPLE 22

Preparation of [5-fluoro-2-methyl- 1-[(4-methylsulfinyl) phenylmethyl]-1H-inden-3-yl] acetaldehyde-o-(2-carboxyethyl) oxime

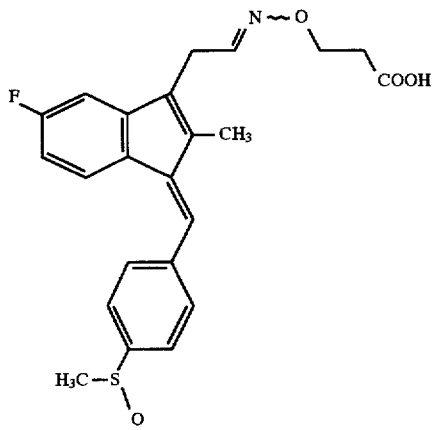

The title compound is prepared by reaction of Z-5-fluoro-2-methyl-1-[(4-methylsulfinyl)phenylmethyl]-1H-inden-3-ylacetaldehyde, prepared as in Example 21, with o-(2-carboxyethyl) hydroxylamine hydrochloride according to the method of Example 1, step 3.

EXAMPLE 23

Preparation of [5-fluoro-2-methyl-1-[(4-methylsulfinyl) phenylmethyl]-1H-inden-3-yl] acetaldehyde-o-(2-hydroxyethyl) oxime

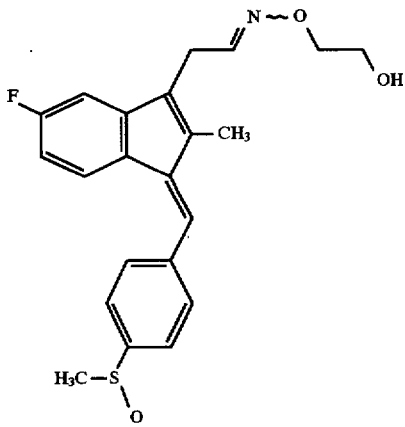

The title compound is prepared by reduction of [5-fluoro-2-methyl-1-[(4-methylsulfinyl)phenylmethyl]-1H-inden-3-yl] acetaldehyde-o-carboxymethyl oxime, prepared as in Example 21 with diborane: THF.

EXAMPLE 24

Preparation of [5-fluoro-2-methyl- 1- [(4-methylsulfinyl) phenylmethyl]-1H-inden-3-ylacetaldehyde-o-(3-hydroxypropyl) oxime

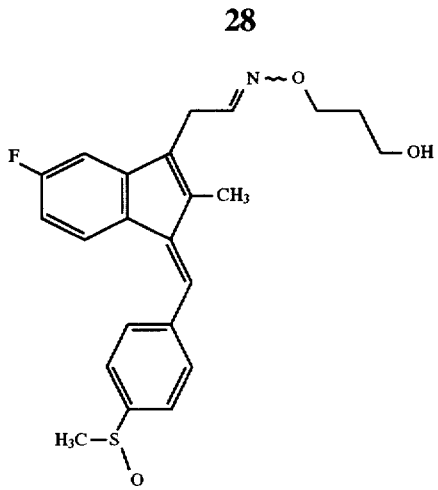

The title compound is prepared by reduction of [5-fluoro-2-methyl-1-[(4-methylsulfinyl)phenylmethyl]-1H-inden-3-yl] acetaldehyde-o-(2-carboxyethyl) oxime, prepared as in Example 22, with diborane: THF.

EXAMPLE 25

Preparation of [5-fluoro-2-methyl-1[(4-methylsulfinyl) phenylmethyl]-1H-inden-3-yl] acetaldehyde-o-(2,3-dihydroxypropyl) oxime

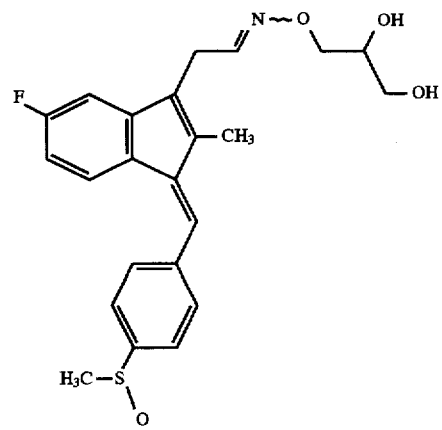

The title compound is prepared by the reaction of [5-fluoro-2-methyl-1-[(4-methylsulfinyl)phenylmethyl]-1H-inden-3-yl] acetaldehyde, prepared as in Example 21, with o-(2,3-dihydroxypropyl) hydroxylamine.

EXAMPLE 26

Preparation of [5-fluoro-2-methyl-1-[(4-methylsulfinyl) phenylmethyl]- 1H-inden-3-yl] acetaldehyde-o-(5-tetrazolylmethyl) oxime

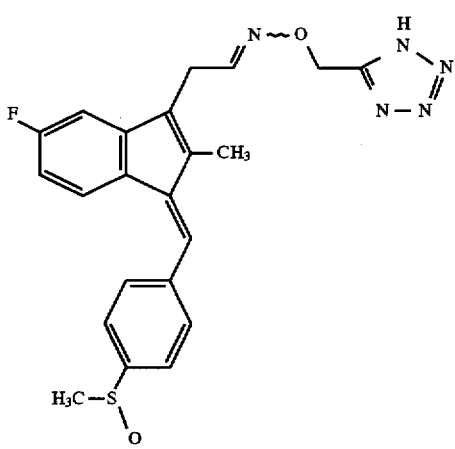

The title compound is prepared by the reaction of [5-fluoro-2-methyl-1-[(4-methylsulfinyl)phenylmethyl]-1H-inden-3-yl] acetaldehyde, prepared as in Example 21, with o-(5-tetrazolylmethyl) hydroxylamine.

We claim:

1. A compound having the formula

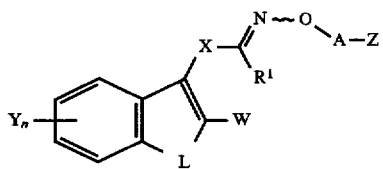

or a pharmaceutically acceptable salt thereof wherein

L is selected from the group consisting of

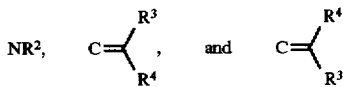

wherein

R² is selected from the group consisting of (a)

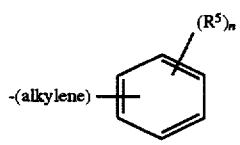

wherein the alkylene portion is of one to six carbon atoms, n is 0, 1, 2, or 3, and R⁵, which may be the same or different at each occurrence, is selected from the group consisting of —OR⁶,
—SR⁶,
halogen,
alkyl of one to six carbon atoms,
haloalkyl of one to six carbon atoms, and
alkoxy of one to six carbon atoms, and (b)

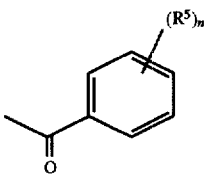

wherein
R5 and n are defined above, (c)

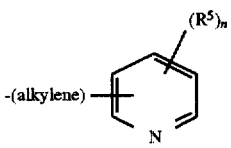

wherein the alkylene portion is of one to six carbon atoms, and R⁵ and n are defined above, and (d)

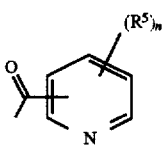

wherein R⁵ and n are defined above;
R³ is selected from the group consisting of
 (a) phenyl,
 (b) phenyl substituted with 1, 2, or 3 groups independently selected from
  —OR⁷,
  —SR⁷,
  halogen,
  alkyl of one to six carbon atoms,
  haloalkyl of one to six carbon atoms, and
  alkoxy of one to six carbon atoms,
 (c) pyridyl, and
 (d) pyridyl substituted with 1, 2, or 3 groups independently selected from
  —OR7,
  —SR⁷,
  halogen,
  alkyl of one to six carbon atoms,
  haloalkyl of one to six carbon atoms, and
  alkoxy of one to six carbon atoms;
Y is selected from the group consisting of
 (a) halogen,
 (b) alkyl of one to six carbon atoms,
 (c) haloalkyl of one to six carbon atoms,
 (d) alkoxy of one to six carbon atoms,
 (e) pyridylmethoxy,
 (f) thiazolylmethoxy,
 (g) benzothiazolylmethoxy,
 (h) quinolylmethoxy, and
 (i) quinolylmethoxy substituted with one or two substitutents selected from
  halogen and
  haloalkyl of one to six carbon atoms, and
n is 0, 1, 2, or 3;

W is selected from the group consisting of
  (a) hydrogen,
  (b) alkyl of one to six carbon atoms,
  (c) hydroxyalkyl of one to six carbon atoms, and
  (d) hydroxy;
A is absent or is selected from the group consisting of
  (a) alkylene of one to six carbon atoms,
  (b) alkylene of one to six carbon atoms substituted with one or two substituents selected from the group consisting of
    —OR$^8$, and
    —COOR$^8$,
  (c) cycloalkylene of three to eight carbon atoms,
  (d) cycloalkylene of three to eight carbon atoms substituted with one or two substituents independently selected from the group consisting of
    alkyl of one to six carbon atoms,
    —OR$^8$, and
    —COOR$^8$,
  (e) heterocycle defined by a cycloalkylene of three to eight carbon atoms wherein one or two of the carbon atoms is replaced with one or two heteroatoms independently selected from O, S, and N,
  (f) heterocycle defined by a cycloalkylene of three to eight carbon atoms wherein one or two of the carbon atoms is replaced with one or two heteroatoms independently selected from O, S, and N, and the ring contains one or two substituents independently selected from alkyl of one to six carbon atoms, —OR$^8$, and —COOR$^8$, and
  (h)

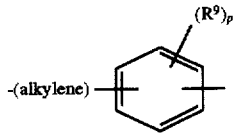

wherein the alkylene portion is of one to six carbon atoms, p is 0, 1, 2, or 3, and R$^9$, which may be the same or different at each occurrence, is selected from the group consisting of
  —OR$^8$,
  —COOR$^8$,
  halogen,
  alkyl of one to six carbon atoms,
  haloalkyl of one to six carbon atoms, and
  alkoxy of one to six carbon atoms;
X is absent or is alkylene of one to six carbon atoms; and
Z is selected from the group consisting of
  (a) hydrogen,
  (b) COM wherein M is selected from the group consisting of
    a pharmaceutically acceptable metabolically cleavable group,
    —OR$^{10}$ wherein R$^{10}$ is selected from the group consisting of
      a pharmaceutically acceptable cation,
      hydrogen,
      alkyl of one to six carbon atoms,
      phenyl,
      phenyl substituted one, two or three substituents selected from the group consisting of
        halogen,
        alkyl of one to six carbon atoms,
        haloalkyl of one to six carbon atoms,
        alkoxy of one to six carbon atoms, and

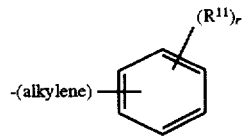

wherein the alkylene portion is of one to six carbon atoms, r is 0, 1, 2, or 3, and R$^{11}$, which may be the same or different at each occurrence, is selected from
    halogen,
    alkyl of one to six carbon atoms,
    haloalkyl of one to six carbon atoms, and
    alkoxy of one to six carbon atoms,
  —O(CH$_2$)$_w$—CH(OR$^{12}$)—CH$_2$OR$^{13}$ wherein w is 1, 2, or 3, R$^{12}$ and R$^{13}$ are independently selected from the group consisting of
    hydrogen,
    alkyl of one to six carbon atoms,
    phenyl,
    phenyl substituted one, two or three substituents selected from
      halogen,
      alkyl of one to six carbon atoms,
      haloalkyl of one to six carbon atoms,
      alkoxy of one to six carbon atoms, and

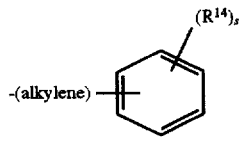

wherein the alkylene portion is of one to six carbon atoms, s is 0, 1, 2, or 3, and R$^{14}$, which may be the same or different at each occurrence, is selected from
    halogen,
    alkyl of one to six carbon atoms,
    haloalkyl of one to six carbon atoms, and
    alkoxy of one to six carbon atoms,
  or R$^{12}$ and R$^{13}$ together with the oxygen atoms to which they are attached define a 5- or 6-membered heterocyclic ring which may be optionally substituted with one or two substituents selected from
    alkyl of one to six carbon atoms,
    haloalkyl of one to six carbon atoms, and
    alkoxy of one to six carbon atoms,
  —NR$^{15}$R$^{16}$ wherein R$^{15}$ and R$^{16}$ are independently selected from
    hydrogen,
    alkyl of one to six carbon atoms,
    hydroxyalkyl of one to six carbon atoms, and
    hydroxy;
  (c) —OR$^{17}$,
  (d) tetrazolyl
  (e) —CH(OR$^{17}$)—CH$_2$OR$^{18}$,
  (f) —CH(OR$^{17}$)—CH$_2$—CH$_2$OR$^{18}$,
  (g) —CH(OR$^{17}$)—CH(OR$^{18}$)—CH$_2$OR$^{19}$, and
  (h) =N—OR$^{17}$; and
R$^1$, R$^4$, R$^6$, R$^7$, R$^8$, R$^{17}$, R$^{18}$, and R$^{19}$ are independently selected at each from
  (a) hydrogen,
  (b) alkyl of one to six carbon atoms,
  (c) phenyl, (d) phenyl substituted one, two or three substituents selected from halogen, alkyl of one to six carbon atoms, haloalkyl of one to six carbon atoms, alkoxy of one to six carbon atoms, and

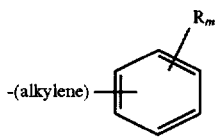

wherein the alkylene portion is of one to six carbon atoms, m is 0, 1, 2, or 3, and R, which may be the same or different at each occurrence, is selected from halogen, alkyl of one to six carbon atoms, haloalkyl of one to six carbon atoms, and alkoxy of one to six carbon atoms.

2. A compound or pharmaceutically acceptable salt thereof as defined by claim 1 having the formula

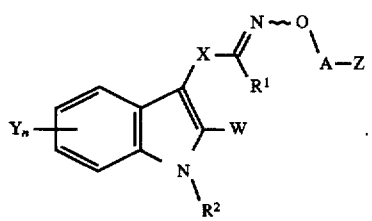

3. A compound or pharmaceutically acceptable salt thereof as defined by claim 2 wherein A is alkylene of one to six carbon atoms.

4. A compound or pharmaceutically acceptable salt thereof as defined by claim 3 wherein Z is selected from the group consisting of (a) —COM wherein M is selected from the group consisting of —$OR^{10}$ wherein $R^{10}$ is selected from a pharmaceutically acceptable cation, hydrogen, and —$O(CH_2)_w$—$CH(OR^{12})$—$CH_2OR^{13}$ wherein w is 1, 2, or 3, and $R^{12}$ and $R^{13}$ are independently selected from hydrogen, and alkyl of one to six carbon atoms, or $R^{12}$ and $R^{13}$ together with the oxygen atoms to which they are attached define a 5- or 6-membered heterocyclic ring which may be optionally substituted with alkyl of one to six carbon atoms, and —$NR^{15}R^{16}$ wherein $R^{15}$ and $R^{16}$ are independently selected from hydrogen, alkyl of one to six carbon atoms, hydroxyalkyl of one to six carbon atoms, and hydroxy;

(b) tetrazolyl (c) —$CH(OR^{17})$—$CH_2OR^{18}$, (d) —$CH(OR^{17})$—$CH_2$—$CH_2OR^{18}$, and (e) —$CH(OR^{17})$—$CH(OR^{18})$—$CH_2OR^{19}$, wherein $R^{17}$, $R^{18}$, and $R^{19}$ are independently selected from hydrogen and alkyl of one to six carbon atoms.

5. A compound as defined by claim 2 having the structure

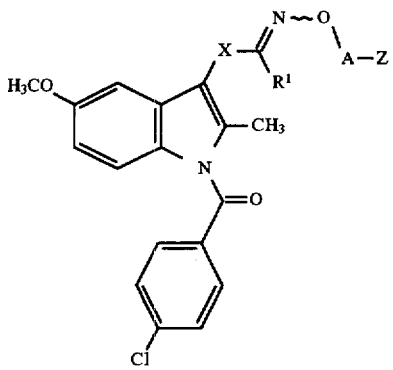

or a pharmaceutically acceptable salt thereof.

6. A compound or pharmaceutically acceptable salt thereof as defined by claim 5 wherein Z is selected from the group consisting of (a) —COM wherein M is selected from the group consisting of —$OR^{10}$ wherein $R^{10}$ is selected from the group consisting of a pharmaceutically acceptable cation, hydrogen, and —$O(CH_2)_w$—$CH(OR^{12})$—$CH_2OR^{13}$ wherein w is 1, 2, or 3, and $R^{12}$ and $R^{13}$ are independently selected from hydrogen, and alkyl of one to six carbon atoms, or $R^{12}$ and $R^{13}$ together with the oxygen atoms to which they are attached define a 5- or 6-membered heterocyclic ring which may be optionally substituted with alkyl of one to six carbon atoms, —$NR^{15}R^{16}$ wherein $R^{15}$ and $R^{16}$ are independently selected from hydrogen, alkyl of one to six carbon atoms, hydroxyalkyl of one to six carbon atoms, and hydroxy;

(b) tetrazolyl (c) —$CH(OR^{17})$—$CH_2OR^{18}$, (d) —$CH(OR^{17})$—$CH_2$—$CH_2OR^{18}$, and (e) —$CH(OR^{17})$—$CH(OR^{18})$—$CH_2OR^{19}$, wherein $R^{17}$, $R^{18}$, and $R^{19}$ are independently selected from hydrogen and alkyl of one to six carbon atoms.

7. A compound or pharmaceutically acceptable salt thereof as defined by claim 6 wherein Z is selected from the group consisting of

—COOH,

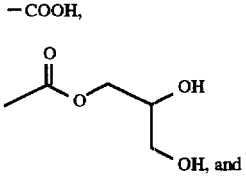

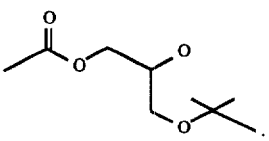

8. A compound as defined by claim 1 having the structure

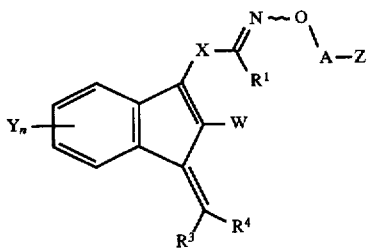

or a pharmaceutically acceptable salt thereof.

9. A compound or pharmaceutically acceptable salt thereof as defined by claim 8 wherein Z is selected from the group consisting of
(a) —COM wherein M is selected from the group consisting of
—$OR^{10}$ wherein $R^{10}$ is selected from
a pharmaceutically acceptable cation and hydrogen, and
—$O(CH_2)_w$—$CH(OR^{12})$—$CH_2OR^{13}$ wherein w is 1, 2, or 3, and $R^{12}$ and $R^{13}$ are independently selected from hydrogen and alkyl of one to six carbon atoms, or $R^{12}$ and $R^{13}$ together with the oxygen atoms to which they are attached define a 5- or 6-membered heterocyclic ring which may be optionally substituted with alkyl of one to six carbon atoms,
—$NR^{15}R^{16}$ wherein $R^{15}$ and $R^{16}$ are independently selected from
hydrogen,
alkyl of one to six carbon atoms,
hydroxyalkyl of one to six carbon atoms, and
hydroxy;
(b) tetrazolyl
(c) —$CH(OR^{17})$—$CH_2OR^{18}$,
(d) —$CH(OR^{17})$—$CH_2$—$CH_2OR^{18}$, and
(e) —$CH(OR^{17})$—$CH(OR^{18})$—$CH_2OR^{19}$,
wherein $R^{17}$, $R^{18}$, and $R^{19}$ are independently selected from hydrogen and alkyl of one to six carbon atoms.

10. A compound as defined by claim 1 having the structure

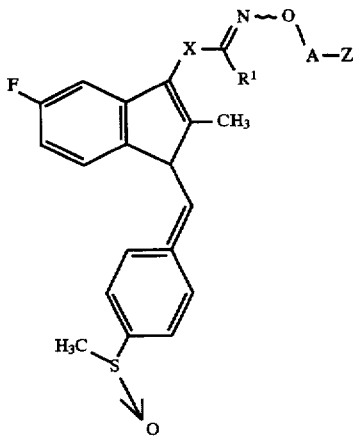

or a pharmaceutically acceptable salt thereof.

11. A compound or pharmaceutically acceptable salt thereof as defined by claim 10 wherein Z is selected from the group consisting of
(a) —COM wherein M is selected from the group consisting of
—$OR^{10}$ wherein $R^{10}$ is selected from
a pharmaceutically acceptable cation and hydrogen, and
—$O(CH_2)_w$—$CH(OR^{12})$—$CH_2OR^{13}$ wherein w is 1, 2, or 3, and $R^{12}$ and $R^{13}$ are independently selected from hydrogen and alkyl of one to six carbon atoms, or $R^{12}$ and $R^{13}$ together with the oxygen atoms to which they are attached define a 5- or 6-membered heterocyclic ring which may be optionally substituted with alkyl of one to six carbon atoms, and
—$NR^{15}R^{16}$ wherein $R^{15}$ and $R^{16}$ are independently selected from
hydrogen,
alkyl of one to six carbon atoms,
hydroxyalkyl of one to six carbon atoms, and
hydroxy;
(b) tetrazolyl
(c) —$CH(OR^{17})$—$CH_2OR^{18}$,
(d) —$CH(OR^{17})$—$CH_2$—$CH_2OR^{18}$, and
(e) —$CH(OR^{17})$—$CH(OR^{18})$—$CH_2OR^{19}$,
wherein $R^{17}$, $R^{18}$, and $R^{19}$ are independently selected from hydrogen and alkyl of one to six carbon atoms.

12. A compound or pharmaceutically acceptable salt thereof as defined by claim 11 wherein Z is selected from the group consisting of

—COOH,

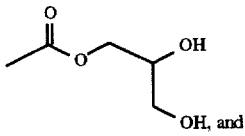

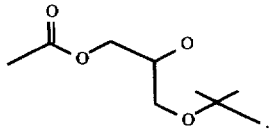

13. A compound or pharmaceutically acceptable salt thereof as defined by claim 1 selected from the group consisting of
(4-chlorobenzoyl-5-methoxy-2-methylindol-3-yl) acetaldehyde-o-carboxymethyl oxime,
(4-chlorobenzoyl-5-methoxy-2-methylindol-3-yl) acetaldehyde-o-4-(2,2-dimethyldioxanylmethyloxycarbonylmethyl) oxime,
(4-chlorobenzoyl-5-methoxy-2-methylindol-3-yl) acetaldehyde-o-4-(2,2-dimethyldioxanylmethyloxycarbonylmethyl) oxime,
(4-chlorobenzoyl-5-methoxy-2-methylindol-3-yl) acetaldehyde-o-(2-carboxyethyl) oxime,
(4-chlorobenzoyl-5-methoxy-2-methylindol-3-yl) acetaldehyde-o-(2-hydroxyethyl) oxime,
(4-chlorobenzoyl-5-methoxy-2-methylindol-3-yl) acetaldehyde-o-(3-hydroxypropyl) oxime,
4-chlorobenzoyl-5-methoxy-2-methylindol-3-yl acetaldehyde-o-(2,3-dihydroxpropyl) oxime,
4-chlorobenzoyl-5-methoxy-2-methylindol-3-yl acetaldehyde-o-(5-tetrazolylmethyl) oxime,
(4-chlorobenzoyl-5-methoxy-2-methylindol-3-yl) acetaldehyde-0-o[(carboxy-2-hydroxyethylamide) methyl] oxime,
(4-chlorobenzoyl-5-methoxy-2-methylindol-3-yl) acetaldehyde-o-(acetohydroxamic acid) oxime,
(4-chlorophenylmethyl-5-methoxy-2-methylindol-3-yl) acetaldehyde-o-carboxymethyl oxime, 1-[1-(4-chlorophenylmethyl-5-methoxy-2-methylindol-3-yl)] propan-2-one- o-carboxymethyl oxime,
(2-pyridylmethyl-5-methoxy-2-methylindol-3-yl) acetaldehyde-o-carboxymethyl oxime,
(3-pyridylmethyl-5-methoxy-2-methylindol-3-yl) acetaldehyde-o-carboxymethyl oxime,
(4-pyridylmethyl-5-methoxy-2-methylindol-3-yl) acetaldehyde-o-carboxymethyl oxime,
(1-t-butoxycarbonyl-5-(quinol-2-ylmethoxy)-2-methylindol-3-yl) acetaldehyde-o-carboxymethyl oxime,
[1-(4-chlorophenylmethyl)-5-(quinol-2-ylmethoxy)-2-methylindol-3-yl] acetaldehyde-o-carboxymethyl oxime,
[4-chorophenylmethyl-5-(benzothiazol-2-ylmethoxy)-2-methylindol-3-yl] acetaldehyde-o-carboxymethyl oxime,
[4-chorophenylmethyl-5-(thiazol-2-ylmethoxy)-2-methylindol-3-yl] acetaldehyde-o-carboxymethyl oxime,
[4-pyridylmethyl-5-(thiazol-2-ylmethoxy)-2-methylindol-3-yl] acetaldehyde-o-carboxymethyl oxime,
[5-fluoro-2-methyl- 1 -[(4-methylsulfinyl)phenylmethyl]-1H-inden-3-yl] acetaldehyde-o-carboxymethyl oxime,
[5-fluoro-2-methyl- 1 -[(4-methylsulfinyl)phenylmethyl]-1H-inden-3-yl] acetaldehyde-o-(2-carboxyethyl) oxime,
[5-fluoro-2-methyl- 1 -[(4-methylsulfinyl)phenylmethyl]-1H-inden-3-yl] acetaldehyde-o-(2-hydroxyethyl) oxime,
[5-fluoro-2-methyl- 1-[(4-methylsulfinyl)phenylmethyl]-1H-inden-3-yl] acetaldehyde-o-(3-hydroxypropyl) oxime,
[5-fluoro-2-methyl- 1-[(4-methylsulfinyl)phenylmethyl]-1H-inden-3-yl] acetaldehyde-o-(2,3-dihydroxypropyl) oxime, and
[5-fluoro-2-methyl- 1-[(4-methylsulfinyl)phenylmethyl]-1H-inden-3-yl] acetaldehyde-o-(5-tetrazolylmethyl) oxime.

14. A compound or pharmaceutically acceptable salt thereof as defined by claim 1 selected from the group consisting of
(4-chlorobenzoyl-5-methoxy-2-methylindol-3-yl) acetaldehyde-o-carboxymethyl oxime,
(4-chlorobenzoyl-5-methoxy-2-methylindol-3-yl) acetaldehyde-o-4-(2,2-dimethyldioxanylmethyloxycarbonylmethyl) oxime, and
(4-chlorobenzoyl-5-methoxy-2-methylindol-3-yl) acetaldehyde-o-4-(2,2-dimethyldioxanylmethyloxycarbonylmethyl) oxime.

15. A method for inhibiting prostaglandin biosynthesis in a mammal in need of such treatment comprising administering to the mammal a therapeutically effective amount of a compound of claim 1.

16. A composition for inhibiting prostaglandin biosynthesis comprising a pharmaceutical carrier and a therapeutically effective amount of a compound of claim 1.

* * * * *